United States Patent [19]

Lavielle et al.

[11] Patent Number: 5,100,881
[45] Date of Patent: Mar. 31, 1992

[54] N-(23-VINCRISTINOYL) AND N-(5'-NORANHYDRO-23-VINBLASTINOYL) COMPOUNDS OF 1-AMINOMETHYLPHOSPHONIC ACID USEFUL FOR THE TREATMENT OF NEOPLASTIC DISEASES

[75] Inventors: Gilbert Lavielle, Celle Saint Cloud; Patrick Hautefaye, Servon Brie Comte Robert; Alain Pierre, Marly Le Roi, all of France

[73] Assignee: Adir et Compagnie, Courbevoie, Cedex, France

[21] Appl. No.: 561,065

[22] Filed: Aug. 1, 1990

[30] Foreign Application Priority Data

Aug. 4, 1989 [FR] France .................. 89 10554

[51] Int. Cl.$^5$ .................. A61K 31/475; C07D 519/04; C07F 9/6561
[52] U.S. Cl. ....................... 514/81; 540/478
[58] Field of Search .............. 540/478; 514/81

[56] References Cited

U.S. PATENT DOCUMENTS

| 3,354,163 | 11/1967 | Gorman | 540/478 |
| 4,210,584 | 7/1980 | Paschal et al. | 540/478 |
| 4,279,915 | 7/1981 | Jovánovics et al. | 514/283 |
| 4,307,100 | 12/1981 | Langlois et al. | 540/478 X |
| 4,522,750 | 6/1985 | Ades et al. | 540/478 X |
| 4,619,935 | 10/1986 | Robinson | 514/283 X |
| 4,923,876 | 5/1990 | Francis et al. | 514/283 |
| 4,946,833 | 8/1990 | Lavielle et al. | 514/81 |

FOREIGN PATENT DOCUMENTS 0117861 9/1984 European Pat. Off. ........ 540/478

*Primary Examiner*—Diana G. Rivers
*Attorney, Agent, or Firm*—Gordon W. Hueschen

[57] ABSTRACT

The invention relates to the compounds of general formula I:

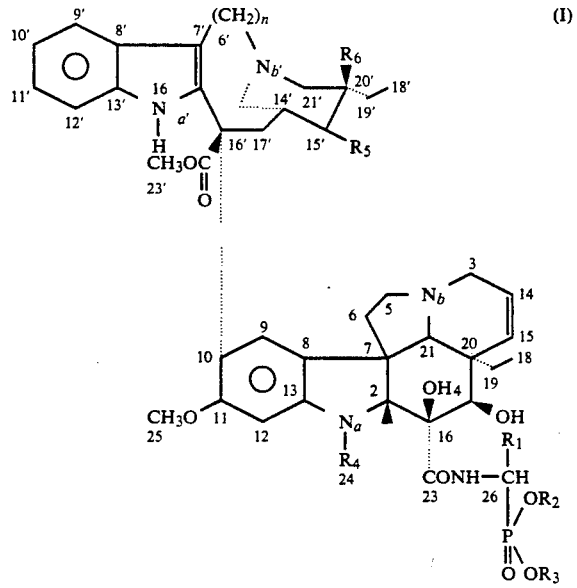

in which:

R$_1$ represents a hydrogen atom, a linear or branched alkyl radical containing from 1 to 6 carbon atoms, a linear or branched alkenyl radical containing from 2 to 6 carbon atoms, an arylalkyl radical having 7 to 10 carbon atoms and which can bear a halogen atom as a substituent on the aromatic ring, a hydroxyl radical or an alkyl or alkoxy radical each containing from 1 to 5 carbon atoms, a 2-indolylmethyl radical, a 4-imidazolylmethyl radical or an alkoxycarbonylmethyl radical containing from 3 to 11 carbon atoms, R$_2$ and R$_3$, which may be identical or different, each represents a linear or branched alkyl radical containing from 1 to 6 carbon atoms, n is equal to 1 or 2, R$_4$ represents a hydrogen atom, a formyl radical or a methyl radical, with the proviso, however, that R$_4$ is never the methyl radical when n is equal to 2, and either R$_5$ and R$_6$ together form a double bond, or R$_5$ represents a hydrogen atom and R$_6$ a hydroxyl radical, in the form of a mixture of diastereoisomers or of pure isomers, their N$_{b'}$-oxides and their addition salts with a pharmaceutically acceptable inorganic or organic acid.

These compounds are antitumor agents.

10 Claims, No Drawings

N-(23-VINCRISTINOYL) AND N-(5'-NORANHYDRO-23-VINBLASTINOYL) COMPOUNDS OF 1-AMINOMETHYLPHOSPHONIC ACID USEFUL FOR THE TREATMENT OF NEOPLASTIC DISEASES

The present invention relates to new N-(23-vincristinoyl) and N-(5'-noranhydro-23-vinblastinoyl) compounds of 1-aminomethylphosphonic acid, to a process for preparing these and to pharmaceutical compositions containing them.

Bisindole alkaloids of the vincristine and navelbine type (Patent EP 010,458) have been used for a long time in therapy, mainly in anticancer chemotherapy. However, these compounds possess high toxicity, which limits their uses. In addition, the activity of navelbine is seen only at a high dosage.

With the object of obtaining compounds having lower toxicity and greater antitumor activity, some N-(4-O-deacetyl-23vincristinoyl) amino compounds have been prepared (patents BE 895,262; BE 813,168). Very recently, Application EP 318,392 has described N-(23-vinblastinoyl) compounds of 1-aminomethylphosphonic acid. These compounds are endowed with very great activity and have lower toxicity (neurotoxicity) compared with the reference products.

Clinical requirements, however, favor the constant development of new anticancer molecules with the object of obtaining improved activity and lower secondary toxicity.

The Applicant has now discovered that some phosphonic compounds of vincristine and of navelbine, of novel structure, possess very advantageous pharmacological properties. In effect, the compounds of the present invention are endowed with much higher antitumor activity than all the vincristine and navelbine compounds already known. In addition, the observed toxicities are significantly lower than those of the reference products.

The subject of the present invention is more especially the 1-aminomethylphosphonic acid compounds of general formula I:

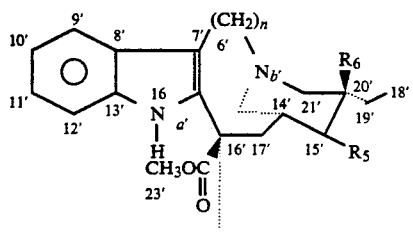

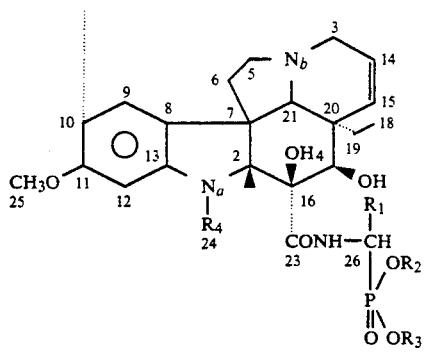

in which:

$R_1$ represents a hydrogen atom, a linear or branched alkyl radical containing from 1 to 6 carbon atoms, a linear or branched alkenyl radical containing from 2 to 6 carbon atoms, an arylalkyl radical having 7 to 10 carbon atoms and which can bear a halogen atom as a substituent on the aromatic ring, a hydroxyl radical or an alkyl or alkoxy radical each containing from 1 to 5 carbon atoms, a 2-indolylmethyl radical, a 4-imidazolylmethyl radical or an alkoxycarbonylmethyl radical containing from 3 to 11 carbon atoms, $R_2$ and $R_3$, which may be identical or different, each represent a linear or branched alkyl radical containing from 1 to 6 carbon atoms, n is equal to 1 or 2, $R_4$ represents a hydrogen atom, a formyl radical or a methyl radical, with the proviso, however, that $R_4$ is never the methyl radical when n is equal to 2, and either $R_5$ and $R_6$ together form a double bond, or $R_5$ represents a hydrogen atom and $R_6$ a hydroxyl radical, in the form of a mixture of diastereoisomers or of pure isomers, their $N_{b'}$-oxides and their addition salts with a pharmaceutically acceptable inorganic or organic acid.

The subject of the present invention is also the process for preparing compounds of general formula I, wherein either an amine, in racemic or optically pure form, of general formula II:

in which the definition of $R_1$, $R_2$ and $R_3$ remains that defined above for the general formula I, is reacted with a compound of formula III:

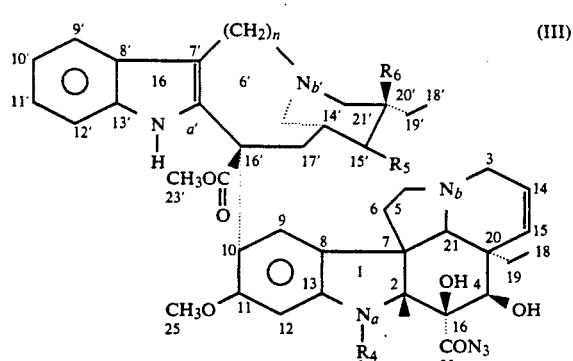

(III)

in which n, $R_5$ and $R_6$ have the meaning defined above for the general formula I and $R_4$ represents a hydrogen atom or a methyl radical, to form, in the form of a mixture of diastereoisomers or of pure isomers, respectively, the compounds of general formula I in which n, $R_1$, $R_2$, $R_3$, $R_5$ and $R_6$ have the meaning defined above and $R_4$ represents a hydrogen atom or a methyl radical, and then, to form the compounds of general formula I in which $R_4$ represents a formyl radical, wherein the compounds of formula Ia:

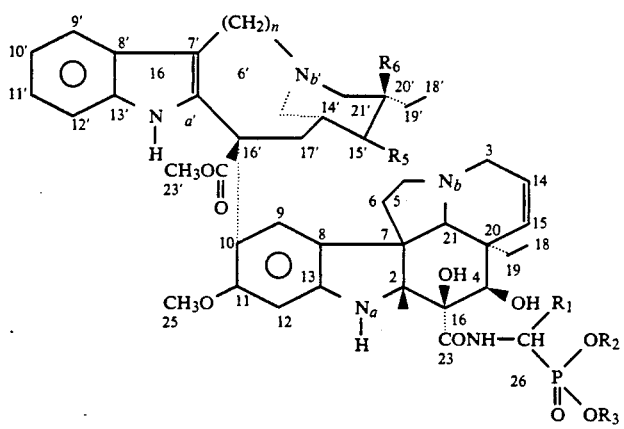

(Ia)

are subjected to the action of formic acid in the presence of acetic anhydride, or a compound, in racemic or optically pure form, of the formula IV:

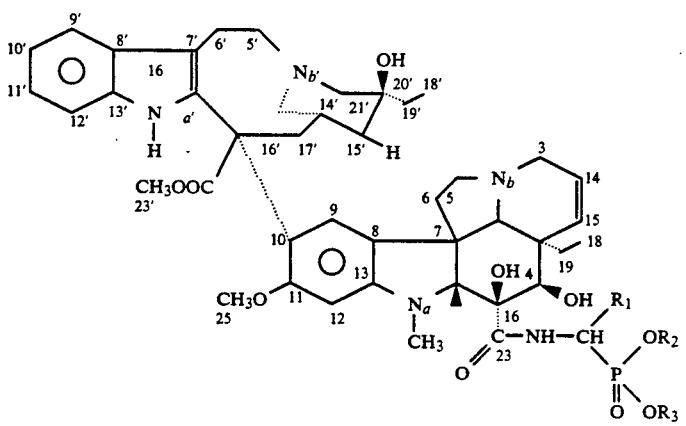

(IV)

in which the definition of $R_1$, $R_2$ and $R_3$ remains identical to that defined above for the formula I, is treated with permanganate ion in an acid medium in an inert solvent, at a temperature of between −40° C. and −75° C., to form the compounds of the general formula I in which n is equal to 2 and $R_4$ represents a formyl radical, and thereafter wherein the compounds of general formula I are salified with a pharmaceutically acceptable inorganic or organic acid, or wherein they are converted to the corresponding $N_{b'}$-oxides by means of a basic organic solvent saturated with oxygen.

1-Aminomethylphosphonates, the compounds of general formula II, may be prepared according to three processes:

either by reduction by means of zinc of the compounds of general formula V:

(V)

in which $R_1$, $R_2$ and $R_3$ have the meaning defined above for the formula I, in solution in formic acid;

or by alkylation of the imines of general formula VI:

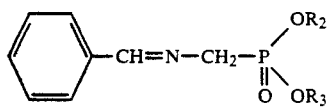 (VI)

in which $R_2$ and $R_3$ have the meaning defined above for the formula I,
by means of an alkylhalide of general formula VII:

$R_1-X$                                           (VII)

in which the definition of $R_1$ remains identical to that given for formula I, according to the method described in Bull. Soc. Chim. Fr. (1978), II, p. 95;

or by the action of diphenylphosphoryl azide (DPPA) on acids of general formula VIII:

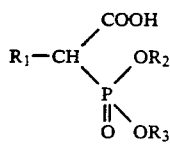 (VIII)

in which $R_1$, $R_2$ and $R_3$ have the meaning defined above for the formula I,
to form the carbamates of general formula IX:

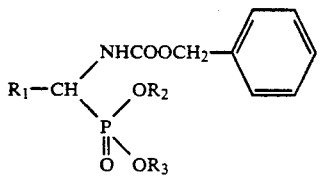 (IX)

in which the definition of $R_1$, $R_2$ and $R_3$ remains identical to that given for the formula I, which are then subjected to a catalytic hydrogenolysis to form the amines of general formula II (Tetrahedron Letters, (1983), 24, (49), p. 5461).

The compounds of general formula V are obtained by the action of hydroxylamine on the ketones of general formula X:

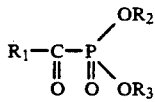 (X)

in which $R_1$, $R_2$ and $R_3$ have the meaning defined above for the formula I, according to the process described in Synthesis (1981), p. 57. The preparation of the compounds of general formula IX is known (Houben Weyl, Methoden der Organischen Chemie, Georg Thiem Verlag, Stuttgart, 5th ed, vol. 12/1, p. 453).

The preparation of the compounds of general formula IV is described in Tetrahedron Letters, (1973), 46, p. 4645.

The formylation of the compounds of formula Ia is performed according to an already known process (J. Org. Chem. (1958), 23, p. 727).

The compounds of formula III are prepared in two steps. The first consists in adding an excess of anhydrous hydrazine to a solution of vincristine or of navelbine base in anhydrous methanol. The compound obtained, of formula XI:

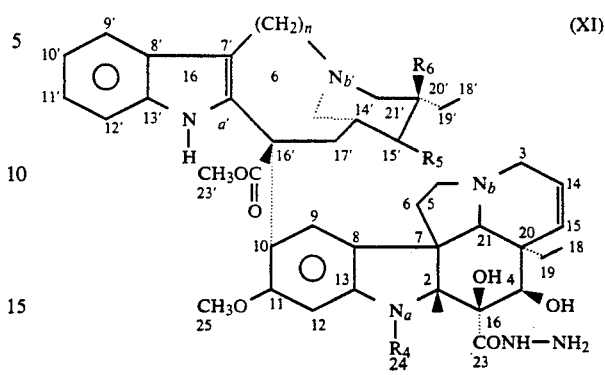 (XI)

in which n, $R_5$ and $R_6$ have the meaning defined above for the general formula I and $R_4$ represents a hydrogen atom or a methyl radical, is then subjected to the action of sodium nitrite in an acid medium to form the compounds of formula III.

The acid used during this latter reaction can be hydrochloric acid. The temperature of the reaction medium is maintained between 0°–5° C.

The acylazides formed are then extracted with a non-water-soluble aprotic solvent, preferably methylene chloride. The compounds of the formula III are preferably not isolated. In effect, the organic solution containing them is concentrated, and the compounds of the formula III are then brought into contact at room temperature with the 1-aminomethylphosphonic acid derivatives of general formula II.

The amines of general formula II may be obtained optically pure, either by fractional crystallization of their salts with an optically pure acid (J. Org. Chem., (1963), 28, p. 2483), or according to the process described in Liebigs Ann. Chem., (1987), p. 45.

The preparation of the compounds of general formula IV is already described in the literature (Patent Application EP 318,392), and the oxidation of these compounds with permanganate ion is performed according to an already known process (Patent Application EP 0,117,861).

The compounds of general formula I may be obtained in the form of pure diastereoisomers by condensation of the corresponding acylazides with an optically pure amine of general formula II, or from a mixture of diastereoisomers which are then separated by high pressure liquid chromatography (HPLC).

The compounds of general formula I are derivatives of 16-decarbomethyoxy-4-O-deacetylvincristine-16-carboxamide and 16-decarbomethoxy-4-O-deacetyl-5'-noranhydrovinblastine-16-carboxamide. However, it is preferable to designate them as N-(23-vincristinoyl) derivatives of 1-aminomethylphosphonic acid and N-(5'-noranhydro-23-vinblastinoyl) derivatives of 1-aminomethylphosphonic acid.

The prefix (+) or (−) used to designate some of the compounds, do not indicate the direction in which they rotate the plane of polarized light, but they designate that the compounds have been obtained from an amine of formula II optically pure (+) or (−).

Among pharmaceutically acceptable acids for the preparation of addition salts with the compounds of general formula I, phosphoric, hydrochloric, citric, oxalic, maleic, sulfuric, tartaric, mandelic, fumaric and methanesulfonic acids, and the like, may be mentioned.

The compounds according to the invention, as well as their addition salts, are endowed with highly advantageous pharmacological properties, and are distinguished from the other vincristine or navelbine compounds already known.

The compounds of the invention were tested for their capacity to prolong the survival of mice bearing tumor cells (P 388 and on a human lung cancer), intraperitoneally according to the protocols recommended by the U.S. National Cancer Institute (Geran R. I. et al., Cancer Chemotherapy Reports, (1972), III, 3, No. 2, p. 1–87), and recognized as representing the antitumor effect in human medicine (Driscoll J. C. S. Cancer Treatment Reports, (1984), 68, No. 1, p. 63–85 and "In Vivo cancer Models" U.S. Department of Health and Human Services NIH Publications No. 84-2635 February 1984).

The compounds of the present invention prove not only capable of retarding the growth of grafted tumors in mice, but also of curing animals. In effect, many complete remissions were observed. In addition, comparative trials with reference products described in the literature—vinblastine, vincristine and navelbine—and with the most active compounds described in Patent Application EP 318,392, demonstrated that the compounds of the invention have much higher activity compared with the compounds already known.

The compounds of the present invention are useful in man and animals in cases of Hodgkin's disease, non-Hodgkin's lymphoma, cancer of the testicle, epithelioma of the breast and ovary, Kaposi's sacroma, choriocarcinoma, histiocytosis, rhabdomyosarcoma, neuroblastoma, Wilims tumor, Ewing's sarcoma, lung cancer, and the like. Other therapeutic applications may also be envisaged for the compounds of the invention. In effect, it is known that bisindole alkaloids and their derivatives are active for the treatment of psoriasis or of some forms of arthritis (U.S. Pat. Nos. 4,208,411 and 3,749,784).

The invention also encompasses pharmaceutical compositions containing as active principle at least one compound of general formula I, one of its optical isomers, one of its addition salts with an inorganic or organic acid or one of its $N_{b'}$- oxides, with one or more suitable non-toxic inert excipients.

The pharmaceutical compositions thereby obtained are advantageously presented in various forms such as, for example, tablets, dragees, hard gelatin capsules, creams for local applications, suppositories, injectable solutions, and the like. They can contain doses from 0.1 to 100 mg of one or more compounds of the invention.

For their therapeutic application, the compounds of the invention, their optical isomers or their addition salts are preferably administered parenterally. Generally speaking, the compounds of the invention may be used in a manner based on the techniques and limitations which are known for therapeutic treatments with other alkaloids of the vinca class.

The dosage can vary widely in accordance with the patient's age and weight, the nature and severity of the condition, the administration route and also the therapeutic scheme used. The total daily doses will generally range from 0.01 to approximately 20 mg/kg.

The compounds of the invention may be used alone or in combination with one or more carcinostatic agents including, for example, alkylating agents, antimetabolites such as methotrexate, 5-fluorouacil, 6-mercaptopurine, 6-thioguanine, cytosine arabinosides and antibiotics such as actinomycin D, daunorubicin and adriamycin, and cis-diamminedichloroplatinum, and the like.

The examples which follow, given without implied limitation, illustrate the invention.

The $^{13}C$ and proton nuclear magnetic resonance (NMR) spectra were recorded at 400 MHz.

EXAMPLE 1

Diethyl N-(4-O-deacetyl-5'-noranhydro-23-vinblastinoyl)-1-amino-2-methylpropylphosphonate

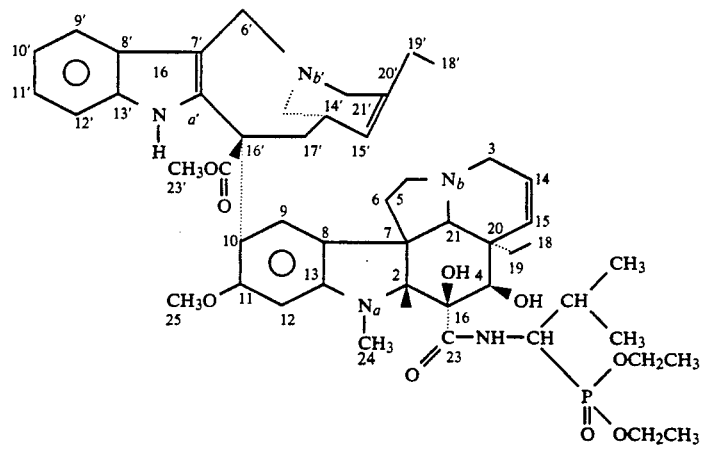

5.20 mmol of sodium nitrite are added to a solution, cooled to 0° C., of 130 ml of N hydrochloric acid containing 2.34 mmol of N-(4-O-deacetyl-5'-noranhydro-23-vinblastinoyl)carbohydrazide. After 10 minutes' contact at 0° C., the pH of the medium is adjusted to 8.8 by means of ice-cold saturated sodium bicarbonate solution, and the product is extracted rapidly by means of 4 times 100 ml of dichloromethane. The combined organic phases are washed by means of saturated sodium chloride solution and dried over anhydrous magnesium sulfate. The organic phase is concentrated to a volume of 50 ml, 3.10 mmol of diethyl 1-amino-2-methylpropylphosphonate (Synthesis (1981), 57) are added and the reaction medium is left for 24 hours at room temperature.

After evaporation of the solvent, the residue is purified by chromatography on a column of silica (230–400 mesh) using a mixture of toluene and ethanol (80V:20V) eluent.

The expected product is collected and recrystallized in a mixture of ethyl ether and petroleum ether (50V:50V).

Yield: 32%

EXAMPLE 2

(+)-[Diethyl N-(4-O-deacetyl-5'-noranhydro-23-vinblastinoyl)-1-amino-2-methylpropylphosphonate]

This compound is prepared according to the method described above, starting with 1.4 g of N-(4-O-deacetyl-5'-noranhydro-23-vinblastinoyl)carbohydrazide and 0.5 g of (+)-diethyl 1-amino-2-methylpropylphosphonate).

After 24 hours' stirring at room temperature, the solvent is separated to obtain 1.45 g of product, which is dissolved in 4 ml of ethanol. This solution is then purified by chromatography using a column containing 500 g of Lichroprep RP 18 (15–25 μm). The column is eluted by means of a mixture of methanol and 0.01M aqueous disodium hydrogen phosphate solution (70V:30V). The flow rate of the mobile phase is set at 28 ml/min. Fractions 540 to 590 are combined and, after condensation under vacuum, the residue is extracted with methylene chloride and the organic phase is then dried over anhydrous magnesium sulfate. After evaporation of the solvent, (+)-[diethyl N-(4-O-deacetyl-5'-noranhydro-23-vinblastinoyl)-1-amino-2-methylpropylphosphonate] is obtained.

Yield: 30%

The corresponding sulfate is formed after the addition of an appropriate quantity of ethanolic sulfuric acid.

The nuclear magnetic resonance spectra given below were prepared with the sulfate of (+)-[diethyl N-(4-O-deacetyl-5'-noranhydro-23-vinblastinoyl)-1-amino-2-methylpropylphosphonate].

| $^{13}C$ nuclear magnetic resonance spectrum (solvent $D_2O$): | | | | | |
|---|---|---|---|---|---|
| 178.4 | ppm $CO_2$ | 82.0 | ppm $C^2$ | 34.1 | ppm $C^{19}$ |
| 175.25/175.3 | ppm CONH | 69.7 | ppm $C^{21}$ | 31.4 | ppm $\underline{C}H(CH_3)_2$ |
| 161.1 | ppm $C^{11}$ | 66.6/66.8 | ppm $(OCH_2CH_3)_2$ | 29.3 | ppm $C^{19'}$ |
| 156.0 | ppm $C^{13}$ | 58.6 | ppm $C^{23'}$ | 20.7/22.5 | ppm $CH(\underline{C}H_3)_2$ |
| 133.8 | ppm $C^{13'}$ | 57.0 | ppm $C^{16'}$ | 18.3 | ppm $(OCH_2\underline{C}H_3)_2$ |
| 133.7 | ppm $C^{15}$ | 56.2 | ppm $C^{25}$ | 13.7 | ppm $C^{18'}$ |
| 130.3 | ppm $C^{2'}$ | 53.4/54.9 | ppm $C^{26}$ | 9.7 | ppm $C^{18}$ |
| 126.4 | ppm $C^{10'}$ | 54.8 | ppm $C^7$ | | |
| 123.7 | ppm $C^{14'}$ | 52.1 | ppm $C^3 + C^5$ | | |
| 123.6 | ppm $C^{14}$ | 49.2 | ppm $C^{21'}$ | | |
| 120.4 | ppm $C^{9'}$ | 46.1 | ppm $C^{3'}$ | | |
| 114.7 | ppm $C^{12'}$ | 45.5 | ppm $C^6$ | | |
| 106.9 | ppm $C^{7'}$ | 45.4 | ppm $C^{20}$ | | |
| 97.5 | ppm $C^{12}$ | 42.1 | ppm $C^{24}$ | | |
| 83.7 | ppm $C^{16}$ | 36.5 | ppm $C^{17'}$ | | |

| Proton magnetic nuclear resonance spectrum (solvent $D_2O$): | | | | | |
|---|---|---|---|---|---|
| 7.84 | ppm | 1H $C^{9'}$—H | 3.73 | ppm | 1H $C^2$—H |
| 7.54 | ppm | 1H $C^{12'}$—H | 3.55 | ppm | 1H $C^{21}$—H |
| 7.35 | ppm | 2H $C^{10'}$—H + $C^{11'}$—H | 3.42/3.94 | ppm | 2H $C^3$—H |
| 6.50 | ppm | 1H $C^{12}$—H | 3.14/3.85 | ppm | 2H $C^5$—H |
| 6.45 | ppm | 1H $C^9$—H | 2.91/3.59 | ppm | 2H $C^{3'}$—H |
| 5.98 | ppm | 1H $C^{14}$—H | 2.87 | ppm | 3H $C^{25}$—H |
| 5.88 | ppm | 1H $C^{15}$—H | 2.60/3.14 | ppm | 2H $C^{17'}$—H |
| 5.83 | ppm | 1H $C^{15'}$—H | 2.34 | ppm | 1H $\underline{C}H(CH_3)_2$ |
| 4.70/4.90 | ppm | 1H $C^{21'}$—H | 2.11 | ppm | 2H $C^{19'}$—H |
| 4.39 | ppm | 1H $C^{26}$—H | 2.02/2.44 | ppm | 2H $C^6$—H |
| 4.24 | ppm | 4H $(O\underline{C}H_2—CH_3)_2$ | 2.02 | ppm | 1H $C^{14'}$—H |
| 4.08 | ppm | 1H $C^{17}$—H | 1.38 | ppm | 6H $(OCH_2\underline{C}H_3)_2$ |
| 3.93 | ppm | 3H $C^{25}$—H | 1.32/1.74 | ppm | 2H $C^{19}$—H |
| 3.80/4.15 | ppm | 2H $C^{5'}$—H | 1.10 | ppm | 3H $C^{18'}$—H |
| 3.79 | ppm | 3H $C^{23'}$—H | 1.09/1.11 | ppm | 6H $CH(\underline{C}H_3)_2$ |
| | | | 0.81 | ppm | 3H $C^{18}$—H |

EXAMPLE 3

(−)-[Diethyl N-(4-O-deacetyl-5'-noranhydro-23-vinblastinoyl)-1-amino-2-methylpropylphosphonate]

This compound is obtained according to the process described for Example 2, but using (−)-(diethyl-1-amino-2-methylpropylphosphonate).

During the purification by chromatography, fractions 400 to 500 are combined and treated as described above.

Yield: 29%

| $^{13}C$ Nuclear magnetic resonance spectrum (solvent $CDCl_3$): | | | |
|---|---|---|---|
| 174.2 ppm $CO_2$— | 110.6 ppm $C^{12'}$ | 44.8 | ppm $C^6$ |
| 172.9 ppm CONH | 93.5 ppm $C^{12}$ | 44.3 | ppm $C^{3'}$ |
| 158.1 ppm $C^{11}$ | 82.9 ppm $C^2$ | 42.9 | ppm $C^{21'}$ |
| 152.8 ppm $C^{13}$ | 80.2 ppm $C^{16}$ | 42.5 | ppm $C^{20}$ |
| 134.3 ppm $C^{13'}$ | 64.6 ppm $C^{21}$ | 39.1 | ppm $C^{24}$ |
| 134.0 ppm $C^{20'}$ | 62.0 ppm $(O\underline{C}H_2CH_3)_2$ | 35.0 | ppm $C^{17'}$ |
| 132.1 ppm $C^{2'}$ | 55.7 ppm $C^{25}$ | 31.1 | ppm $C^{19}$ |
| 129.5 ppm $C^{15}$ | 54.9 ppm $C^{16'}$ | 29.8 | ppm $\underline{C}H(CH_3)_2$ |

-continued

| $^{13}C$ Nuclear magnetic resonance spectrum (solvent $CDCl_3$): | | | |
|---|---|---|---|
| 128.5 ppm $C^{8'}$ | 53.6 ppm $C^7$ | 27.7 ppm $C^{19'}$ | |
| 124.5 ppm $C^{14}$ | 53.4 ppm $C^{6'}$ | 20.8/18.2 ppm $CH(\underline{C}H_3)_2$ | |
| 122.7 ppm $C^{10'}$ | 52.2 ppm $C^{23'}$ | 16.3 ppm $(OCH_2\underline{C}H_3)_2$ | |
| 120.0 ppm $C^{11'}$ | 50.3 ppm $C^3$ | 12.0 ppm $C^{18'}$ | |
| 118.3 ppm $C^{9'}$ | 49.8 ppm $C^{26}$ | 8.4 ppm $C^{18}$ | |
| 118.2 ppm $C^{7'}$ | 49.0 ppm $C^5$ | | |

EXAMPLE 4

(+)-[Diethyl N-($N_a$-deformyl-4-O-deacetyl-23-vincristinoyl)-1-amino-2-methylpropylphosphonate]

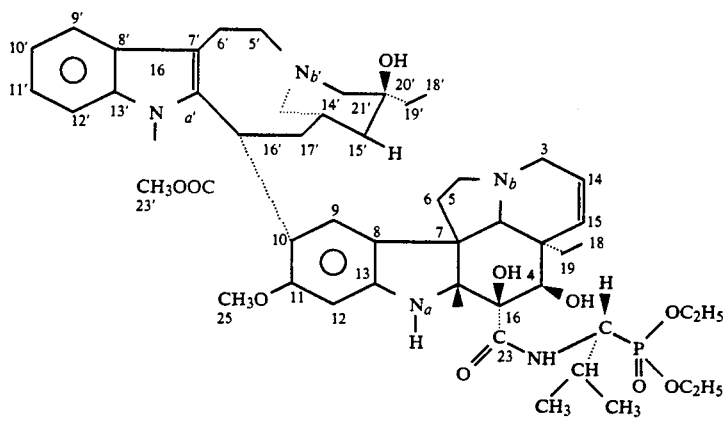

4,6 g of $N_a$-deformyl-4-O-deacethylvincristine azide, in solution in 50 ml of dichloromethane, are stirred for 24 hours at room temperature in the presence of 1.2 g of (+)-(diethyl 1-amino-2-methylpropylphosphonate) to obtain the expected product. The (+)-[diethyl N-($N_a$-deformyl-4-O-deacetyl-23-vincristinoyl)-1-amino-2-methylpropylphosphonate] is then purified by chromatography according to the process described in Example 2.

Yield: 27%

| Proton nuclear magnetic resonance spectrum (solvent $CDCl_3$): | | | |
|---|---|---|---|
| 8.5 | ppm 1H NH | 2.80/3.30 | ppm 2H $C^5$—H |
| 8.1 | ppm 2H NH,NHCO | 2.74 | ppm 2H $C^{21'}$—H |
| 7.50 | ppm 1H $C^{9'}$—H | 2.64 | ppm 2H $C^{21}$—H |
| 7.20/7.12 | ppm 3H $C^{10'}$—H + $C^{11'}$—H + $C^{12'}$—H | 2.40/3.21 | ppm 2H $C^{3'}$—H |
| 6.65 | ppm 1H $C^9$—H | 2.45/3.10 | ppm 2H $C^3$—H |
| 6.27 | ppm 1H $C^{12}$—H | 2.35/4.03 | ppm 2H $C^{17'}$—H |
| 5.85 | ppm 1H $C^{14}$—H | 2.34 | ppm 1H $\underline{C}H(CH_3)_2$ |
| 5.70 | ppm 1H $C^{15}$—H | 1.90/2.10 | ppm 2H $C^6$—H |
| 4.42 | ppm 1H $C^{26}$—H | 1.51 | ppm 2H $C^{15'}$—H |
| 4.10 | ppm 5H $C^4$—H + $(O\underline{C}H_2CH_3)_2$ | 1.40 | ppm 2H $C^{19}$—H |
| 3.91 | ppm 1H $C^2$—H | 1.38 | ppm 6H $(OCH_2—\underline{C}H_3)_2$ |
| 3.75 | ppm 3H $OCH_3$ | 1.25/1.60 | ppm 2H $C^{19'}$—H |
| 3.65 | ppm 3H $C^{23'}$—H | 1.14 | ppm 6H $CH(\underline{C}H_3)_2$ |
| 3.31 | ppm 2H $C^{5'}$—H | 0.90 | ppm 6H $C^{18}$—H + $C^{18'}$—H |

EXAMPLE 5

(−)-[Diethyl N-($N_a$-deformyl-4-O-deacetyl-23-vincristinoyl)-1-amino-2-methyl-propylphosphonate]

This compound was prepared according to the process described in Example 4, but using (−)-(diethyl 1-amino-2-methylphosphonate). The compound obtained was purified by chromatography according to the method described in Example 3.

Yield: 29%

| Proton nuclear magnetic resonance spectrum (solvent $CDCl_3$): | | | |
|---|---|---|---|
| 8.7 | ppm 1H NH | 2.75 | ppm 2H $C^{21'}$—H |
| 8.03 | ppm 1H NHCO | 2.70 | ppm 2H $C^{21}$—H |
| 7.48 | ppm 1H $C^{9'}$—H | 2.41/3.15 | ppm 2H $C^3$—H |
| 7.17/7.15/7.09 | ppm 3H $C^{10'}$—H + $C^{11'}$—H + $C^{12'}$—H | 2.35/4.00 | ppm 2H $C^{17'}$—H |
| 6.63 | ppm 1H $C^9$—H | 2.35 | ppm 1H $\underline{C}H(CH_3)_2$ |
| 6.27 | ppm 1H $C^{12}$—H | 1.88/2.10 | ppm 2H $C^6$—H |
| 5.91 | ppm 1H $C^{14}$—H | 1.54 | ppm 2H $C^{15'}$—H |

| -continued | | | |
|---|---|---|---|
| Proton nuclear magnetic resonance spectrum (solvent CDCl$_3$): | | | |
| 5.79 | ppm 1H C$^{15}$—H | 1.44 | ppm 2H C$^{19}$—H |
| 4.50 | ppm 1H C$^{26}$—H | 1.42 | ppm 6H (OCH$_2$—H$_3$)$_2$ |
| 4.13 | ppm 1H C$^{4}$—H | 1.25/1.65 | ppm 2H C$^{19'}$—H |
| 4.08 | ppm 4H (OC$\underline{H}_2$CH$_3$)$_2$ | 1.15/1.11 | ppm 6H CH(C$\underline{H}_3$)$_2$ |
| 3.91 | ppm 1H C$^{2}$—H | 0.98 | ppm 3H C$^{18'}$—H |
| 3.75 | ppm 3H OCH$_3$ | 0.91 | ppm 3H C$^{18}$—H |
| 3.63 | ppm 3H C$^{23'}$—H | | |
| 3.28 | ppm 2H C$^{5'}$—H | | |
| 2.83/3.28 | ppm 2H C$^{5}$—H | | |

EXAMPLE 6

(+)-[Diethyl
N-(4-O-deacetyl-23-vincristinoyl)-1-amino-2-methyl-
propylphosphonate]

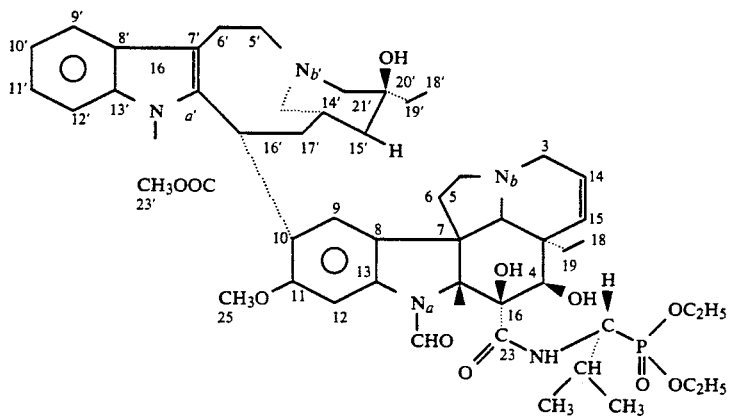

3.7 g of the compound of Example 4 are dissolved in a mixture of 22 ml of formic acid and 4 ml of acetic anhydride. The medium is maintained for 1 hour at room temperature and then treated with 120 ml of ice-cold water. The pH of the solution is then brought to 9 by adding ice-cold ammonia solution. The medium is extracted twice with dichloromethane. The organic phase is washed with saline solution, then once with water and dried over anhydrous magnesium sulfate. The medium is concentrated under vacuum. 3.5 g of the expected product are obtained, which produced is purified by preparative HPLC (500 g of Lichroprep RP 18; eluent 10$^{-2}$M Na$_2$HPO$_4$/methanol, 40V:60V). Fractions 75 to 140 are recovered, the solvent is concentrated under vacuum and the residual aqueous phase is extracted with dichloromethane. The organic phase is washed with water, dried and concentrated under vacuum. 500 mg of pure product are obtained.

Yield: 13%

| Proton nuclear magnetic resonance spectrum (solvent CDCl$_3$): | | | |
|---|---|---|---|
| 9.5 | ppm | 1H CHO | 3.5/4.0 ppm 2H C$^{5}$—H |
| 8.5 | ppm | 1H NH | 3.31 ppm 2H C$^{5'}$—H |
| 8.1 | ppm | 3H NH,NHCO, C$^{9}$—H | 2.45/3.10 ppm 2H C$^{3}$—H |
| 7.65 | ppm | 1H C$^{12}$—H | 2.40/3.21 ppm 2H C$^{3'}$—H |
| 7.50 | ppm | 1H C$^{9'}$—H | 2.35/4.03 ppm 2H C$^{17'}$—H |
| 7.40 | ppm | } 3H C$^{10'}$—H + C$^{11'}$—H + C$^{12'}$—H | 2.14 ppm 1H C$\underline{H}$(CH$_3$)$_2$ |
| 7.12 | ppm | | 1.90/2.50 ppm 2H C$^{6}$—H |
| 7.02 | ppm | | 1.51 ppm 2H C$^{15'}$—H |
| 5.85 | ppm | 1H C$^{14}$—H | 1.40 ppm 2H C$^{19}$—H |
| 5.70 | ppm | 1H C$^{15}$—H | 1.38 ppm 6H (OCH$_2$—C$\underline{H}_3$)$_2$ |
| 4.42 | ppm | 1H C$^{26}$—H | 1.25/1.60 ppm 2H C$^{19'}$—H |
| 4.36 | ppm | 2H C$^{21'}$ | 1.14 ppm 6H CH(C$\underline{H}_3$)$_2$ |
| 4.10 | ppm | 5H C$^{4}$—H + (OC$\underline{H}_2$CH$_3$)$_2$ | 0.90 ppm 6H C$^{18'}$—H |
| 4.02 | ppm | 2H C$^{21}$ | 0.72 ppm 3H C$^{18}$—H |
| 3.91 | ppm | 1H C$^{2}$—H | |
| 3.75 | ppm | 3H C$^{25}$—H | |
| 3.65 | ppm | 3H C$^{23'}$—H | |

EXAMPLE 7

(−)-[Diethyl
N-(4-O-deacetyl-23-vincristinoyl)-1-amino-2-methyl-
propylphosphonate]

This compound is obtained according to the process described in Example 6, but using the compound of Example 5.

The compound obtained was purified by chromatography according to the method described in Example 6, but recovering fractions 200 to 290.

| Proton nuclear magnetic resonance spectrum (solvent CDCl$_3$): | | | |
|---|---|---|---|
| 8.12 | ppm 1H C$^{12}$—H | 3.25/3.9 | ppm 2H C$^3$—H |
| 7.68 | ppm 1H C$^9$—H | 2.83/3.8 | ppm 2H C$^{3'}$—H |
| 7.53 | ppm 1H C$^{9'}$—H | 2.27/3.9 | ppm 2H C$^{17'}$—H |
| 7.44 | ppm 1H C$^{12'}$—H | 2.12 | ppm 1H CH(CH$_3$)$_2$ |
| 7.12 | ppm 1H C$^{10'}$—H | 1.78/2.51 | ppm 2H C$^6$—H |
| 7.02 | ppm 1H C$^{11'}$—H | 1.47 | ppm 2H C$^{15'}$—H |
| 5.91 | ppm 2H C$^{14}$—H + C$^{15}$—H | 1.44 | ppm 2H C$^{19'}$—H |
| 4.45 | ppm 1H C$^2$—H | 1.40/1.70 | ppm 2H C$^{19}$—H |
| 4.20 | ppm 3H C$^{26}$—H + C$^{21'}$—H | 1.31 | ppm 6H CH(CH$_3$)$_2$ |
| 4.10 | ppm 5H C$^{21}$—H + (OCH$_2$—CH$_3$)$_2$ | 1.10 | ppm 1H C$^{14'}$—H |
| 3.85 | ppm 1H C$^{17}$—H | 0.95/1.02 | ppm 6H (OCH$_2$CH$_3$)$_2$ |
| 3.80 | ppm 3H C$^{25}$—H | 0.86 | ppm 3H C$^{18}$—H |
| 3.63 | ppm 3H C$^{23'}$—H | 0.70 | ppm 3H C$^{18'}$—H |
| 3.6/3.9 | ppm 2H C$^{5'}$—H | | |
| 3.55/4.1 | ppm 2H C$^5$—H | | |
| 3.3/4.44 | ppm 2H C$^{6'}$—H | | |

| $^{13}$C nuclear magnetic resonance spectrum (solvent CDCl$_3$): | | | |
|---|---|---|---|
| 173.3 | ppm C$^{23'}$ | 56.1 | ppm C$^{5'}$ |
| 169.5 | ppm C$^{23}$ | 55.1 | ppm C$^{16'}$ |
| 161.5 | ppm C$^{24}$ | 52.3 | ppm C$^{23'}$ |
| 156.7 | ppm C$^{11}$ | 50.4 | ppm C$^7$ |
| 141.2 | ppm C$^{13}$ | 49.4 | ppm C$^3$ |
| 136.0 | ppm C$^{13'}$ | 48.9/50.4 | ppm C$^{26}$ |
| 132.5 | ppm C$^{15}$ | 48.8 | ppm C$^5$ |
| 130.4 | ppm C$^{2'}$ | 44.1 | ppm C$^{3'}$ |
| 128.3 | ppm C$^{8'}$ | 41.8 | ppm C$^{20}$ |
| 126.4 | ppm C$^{10}$ | 38.8 | ppm C$^6$ |
| 123.7 | ppm C$^8$ + C$^9$ | 35.9 | ppm C$^{15'}$ |
| 121.7 | ppm C$^{14}$ + C$^{10'}$ | 35.1 | ppm C$^{17'}$ |
| 118.6 | ppm C$^{11'}$ | 33.9 | ppm C$^{19'}$ |
| 117.7 | ppm C$^{9'}$ | 31.4 | ppm C$^{19}$ |
| 113.0 | ppm C$^{7'}$ | 29.4 | ppm CH(CH$_3$)$_2$ |
| 112.2 | ppm C$^{12'}$ | 26.2 | ppm C$^{14'}$ |
| 100.7 | ppm C$^{12}$ | 20.4 | ppm C$^{6'}$ |
| 82.3 | ppm C$^{16}$ | 17.4/20.1 | ppm (OCH$_2$CH$_3$)$_2$ |
| 72.3 | ppm C$^{17}$ | 16.2 | ppm CH(CH$_3$)$_2$ |
| 69.4 | ppm C$^2$ | 7.23 | ppm C$^{18'}$ |
| 66.5 | ppm C$^{20'}$ | 6.15 | ppm C$^{18}$ |
| 64.3 | ppm C$^{21'}$ | | |
| 61.6/62 | ppm (OCH$_2$—CH$_3$)$_2$ | | |
| 60.3 | ppm C$^{21'}$ | | |
| 56.2 | ppm C$^{25}$ | | |

EXAMPLE 8

(+)-[Diethyl N-(N$_a$-deformyl-4-O-deacetyl-23-vincristinoyl)-1-aminoethylphosphonate]

This compound was prepared according to the process described in Example 4, but using (+)-(diethyl 1-aminoethylphosphonate).

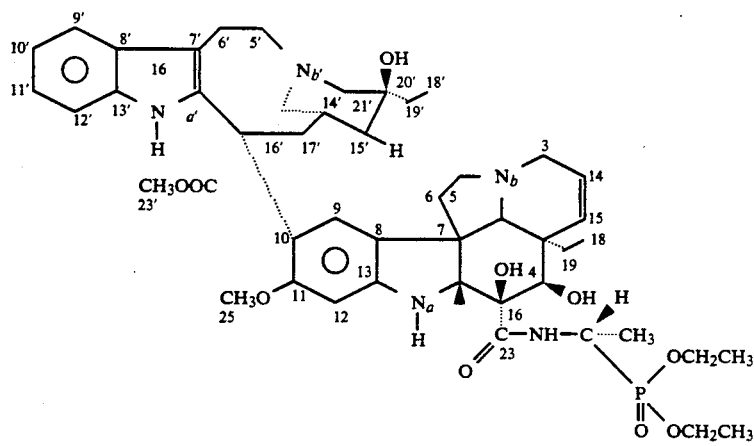

| Proton nuclear magnetic resonance spectrum (solvent CDCl₃): | | | |
|---|---|---|---|
| 7.62 | ppm 1H $C^{9'}$—H | 2.90/3.35 | ppm 2H $C^3$—H |
| 7.35 | } ppm 3H $C^{10'}$—H + $C^{11'}$—H + $C^{12'}$—H | 2.80 | ppm 2H $C^{21'}$—H |
| 7.15 | | 2.60 | ppm 2H $C^{21}$—H |
| 7.08 | | 2.20/3.10 | ppm 2H $C^{3'}$—H |
| 6.60 | ppm 1H $C^9$—H | 2.40/3.20 | ppm 2H $C^5$—H |
| 6.10 | ppm 1H $C^{12}$—H | 2.50/4.00 | ppm 2H $C^{17'}$—H |
| 5.80 | ppm 1H $C^{14}$—H | 1.60/2.00 | ppm 2H $C^6$—H |
| 5.60 | ppm 1H $C^{15}$—H | 1.60 | ppm 2H $C^{15'}$—H |
| 4.50 | ppm 1H $C^{26}$—H | 1.50 | ppm 3H $\underline{CH_3}$—$CH_2$ |
| 4.18 | ppm 1H $C^4$—H | 1.45 | ppm 2H $C^{19}$—H |
| 4.11 | ppm 4H $(O\underline{CH_2}CH_3)_2$ | 1.30 | ppm 6H $(OCH_2\underline{CH_3})_2$ |
| 3.85 | ppm 1H $C^2$—H | 1.30/1.70 | ppm 2H $C^{19'}$—H |
| 3.80 | ppm 3H $C^{25}$—H | 0.95 | ppm 3H $C^{18'}$—H |
| 3.60 | ppm 3H $C^{23'}$—H | 0.80 | ppm 3H $C^{18}$—H |
| 3.35 | ppm 2H $C^{5'}$—H | | |

EXAMPLE 9

(+)-[Diethyl N-(4-O-deacetyl-23-vincristinoyl)-1-aminoethylphosphonate]

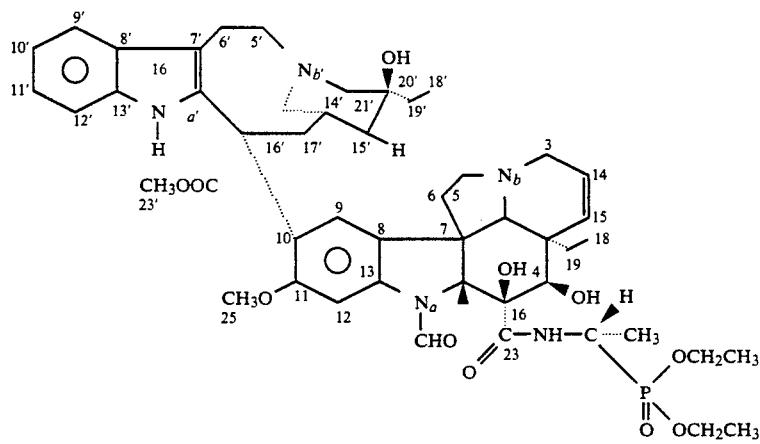

Process A

This compound was prepared from the compound of Example 8, using the process described in Example 6.

being outgassed by passing argon bubbled through at room temperature.

A solution of 103 mg of potassium permanganate and 290 mg of 18-crown-6 crown ether in 12 of methylene chloride is added dropwise.

When the reaction is complete, the reaction medium is poured into an ice-cold solution of 19 ml of 5% strength sodium metabisulfite and 10 ml of concentrated ammonia solution.

| Proton nuclear magnetic resonance spectrum (solvent CDCl₃): | | | |
|---|---|---|---|
| 8.00 | ppm 1H $C^{12}$—H | 3.40/4.10 | ppm 2H $C^6$—H |
| 7.70 | ppm 1H $C^9$—H | 3.30/3.80 | ppm 2H $C^{5'}$—H |
| 7.55 | ppm 1H $C^{9'}$—H | 3.30/3.75 | ppm 2H $C^3$—H |
| 7.50 | ppm 1H $C^{12'}$—H | 2.80/3.70 | ppm 2H $C^{3'}$—H |
| 7.10 | ppm 2H $C^{10'}$—H + $C^{11'}$—H | 2.30/3.90 | ppm 2H $C^{17'}$—H |
| 5.95 | ppm 1H $C^{14}$—H | 1.70/2.40 | ppm 2H $C^6$—H |
| 5.90 | ppm 1H $C^{15}$—H | 1.50 | ppm 2H $C^{15'}$—H |
| 4.30 | ppm 1H $C^2$—H | 1.40 | ppm 3H $\underline{CH_3}$—CH |
| 4.25 | ppm 1H $C^{26}$—H | 1.40/1.70 | ppm 2H $\overline{C^{19}}$—H |
| 4.20 | ppm 3H $C^{21}$—H + $C^{21'}$—H | 1.30/1.60 | ppm 2H $C^{19'}$—H |
| 4.05 | ppm 4H $(O—\underline{CH_2}—CH_3)_2$ | 1.05 | ppm 6H $(OCH_2—\underline{CH_3})$ |
| 3.70 | ppm 3H $C^{25}$—H | 1.00 | ppm 1H $C^{14'}$—H |
| 3.65 | ppm 3H $C^{23'}$—H | 0.95 | ppm 3H $C^{18}$—H |
| 3.40/3.90 | ppm 2H $C^{5'}$—H | 0.90 | ppm 3H $C^{18'}$—H |

Process B

A solution of 300 mg of (+)-[diethyl N-(4-O-deacetyl-23-vinblastinoyl)-1-aminoethylphosphonate] sulfate (Patent Application EP 318,392) is 28 ml of methylene chloride and 4 ml of acetic acid is cooled to 70° C. after The resulting emulsion is filtered on Celite and the filtrate is extracted by means of 3 times 25 ml of methylene chloride.

The organic combined organic phases are washed by means of 10 ml of water and dried over magnesium sulfate; evaporation of the solvent yields the expected base.

To obtain the corresponding sulfate, a suitable quantity of ethanolic sulfuric acid is added.

Overall yield 20%.

PHARMACOLOGICAL STUDY

EXAMPLE 10

Antitumor activity against P 388 leukemia in mice

Mice (n=6), strain $B_6D_2F_1$ ($F_1$:C57Bl$_6$×DBA$_2$), received intraperitoneally on day zero 0.4 ml of physiological saline containing $10^6$ leukemic cells in suspension. The products under examination were administered i.p. to the "test" groups one day after inoculation of the leukemic cells. The mortality of the animals in the "test" and "control" groups are recorded for 60 days after the inoculation. Table I shows the number of survivors noted after 30 days and 60 days of observation. After 60 days of observation, the animals which survived were considered to be in long-term remission. Table II shows the percentage values for the mean survival time (MST) of the test groups T over the mean survival time of the untreated control group C. T/C (MST) values above 125% signify antitumor activity.

As shown by the results in Tables I and II, the compounds of the invention posses better antitumor activity compared with the reference compounds vinblastine and vincristine, and also compared with (+)-[diethyl N-(4-O-deacetyl-23-vinblastinoyl)-1-amino-2-methyl-propylphosphonate] (NDVAMPP) which is the most active compound among the products described in Patent Application EP 318,392. In effect, the compound of Example 6, for a dose twice as small as that of NDVAMPP, is curative for all the mice.

TABLE I

| COMPOUND | DOSE mg/kg | SURVIVORS 30 days | 60 days |
|---|---|---|---|
| VINBLASTINE | 3 mg/kg | 1/6 | 1/6 |
| VINCRISTINE | 3 mg/kg | 0/6 | 0/6 |
| NDVAMPP | 0.2 mg/kg | 5/6 | 5/6 |
| EXAMPLE 6 | 0.1 mg/kg | 6/6 | 6/6 |

TABLE II

| COMPOUND | DOSE mg/kg | T/C % |
|---|---|---|
| VINBLASTINE | 3 mg/kg | 245 |
| VINCRISTINE | 3 mg/kg | 192 |
| NDVAMPP | 0.2 mg/kg | 405 |
| EXAMPLE 6 | 0.1 mg/kg | >550 |

EXAMPLE 11

Antitumor activity on a human lung cancer grafted into NUDE (LX1) mice

The NUDE mice are treated when the size of the tumor is 5 mm × 5mm. The compounds are administered i.p. at D0, D3, D6 and D9. As shown by the results in Table III, the compounds of the invention possess very considerable antitumor activity, whereas vinblastine exhibits very little activity.

TABLE III

| COMPOUND | DOSE mg/kg | SGD* | T/C** |
|---|---|---|---|
| VINBLASTINE | 1 | 1.5 (+) | 56 (+) |

TABLE III-continued

| COMPOUND | DOSE mg/kg | SGD* | T/C** |
|---|---|---|---|
| EXAMPLE 2 | 0.70 | 3.1 (+++) | 21 (+++) |

*SGD: Standard Growth Delay
**Tumor volume treated animals/tumor volume control animals

EXAMPLE 12

In vitro cytotoxicity

L1210 cells in an exponential growth phase are diluted with complete culture medium (RPMI containing 10% of fetal calf serum, 2 nM glutamine, 50 units/ml of penicillin, 50 µg/ml of streptomycin and 10 nM HEPES) so as to obtain a density of $10^4$ cells/ml.

The products are tested at 9 concentrations (serial 2-fold dilutions) and incubated with the cells for 48 hours. The number of viable cells is then quantified by a colorimetric assay, the Microculture Tetrazolium Assay).

The results are expressed as an $IC_{50}$, the concentration of the product which 50% inhibits the proliferation of the control cells.

As demonstrated by the results in Table IV, the compounds of the invention possess better antitumor activity than the reference compounds vinblastine and vincristine.

TABLE IV

| COMPOUND | $IC_{50}$ |
|---|---|
| Vincristine | 4.20 ± 0.7 nM |
| Vinblastine | 2.30 ± 0.5 nM |
| Example 6 | 0.35 ± 0.09 nM |

PHARMACEUTICAL PREPARATION

EXAMPLE 13

Lyophilized powder for an injectable preparation containing 0.2 mg of (+)-[diethyl N-(4-O-deacetyl-23-vincristinoyl)-1-amino-2-methyl-propylphosphonate]

| | |
|---|---|
| (+)-[Diethyl N-(4-O-deacetyl-23-vincristinoyl)-1-amino-2-methylpropylphosphonate] | 0.2 mg |
| Lactose, anhydrous | 10.0 mg | per bottle of powder.

We claim:

1. A compound of formula I:

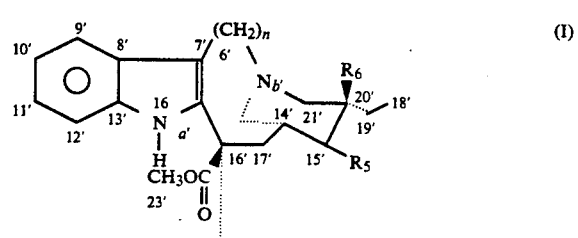

-continued

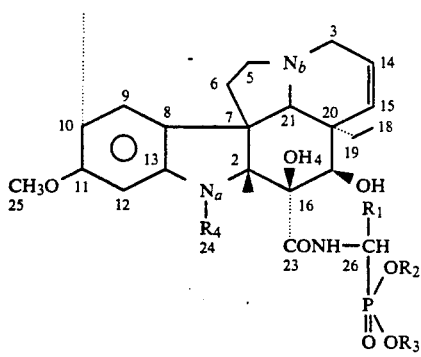

in which:

R₁ represents a hydrogen atom, a linear or branched alkyl radical containing from 1 to 6 carbon atoms, a linear or branched alkenyl radical containing from 2 to 6 carbon atoms, an arylalkyl radical having 7 to 10 carbon atoms and which can bear a halogen atom as a substituent on the aromatic ring, a hydroxyl radical or an alkyl or alkoxy radical each containing from 1 to 5 carbon atoms, a 2-indolylmethyl radical, a 4-imidazolylmethyl radical or an alkoxycarbonylmethyl radical containing from 3 to 11 carbon atoms, R₂ and R₃, which may be identical or different, each represent a linear or branched alkyl radical containing from 1 to 6 carbon atoms, n is equal to 1 or 2, R₄ represents a hydrogen atom, a formyl radical or a methyl radical, with the proviso, however, that R₄ is never the methyl radical when n is equal to 2, and either R₅ and R₆ together form a double bond, or R₅ represents a hydrogen atom and R₅ a hydroxyl radical, in the form of a mixture of diastereoisomers or of pure isomers, their N_b'-oxides and their addition salts with a pharmaceutically acceptable inorganic or organic acid.

2. A compound of claim 1 being diethyl N-(4-O-deacetyl-5'-noranhydro-23-vinblastinoyl)-1-amino-2-methylpropylphosphonate, in the form of a mixture of diastereoisomers or of pure isomers, or an addition salt thereof with a pharmaceutically acceptable inorganic or organic acid.

3. A compound of claim 1 being (+)-[diethyl N-(N_a-deformyl-4-O-deacetyl-23-vincristinoyl)-1-amino-2-methylpropylphosphonate], or an addition salt thereof with a pharmaceutically acceptable inorganic or organic acid.

4. A compound of claim 1 being (+)-[diethyl N-(4-O-deacetyl-23-vincristinoyl)-1-amino-2-methylpropylphosphonate], or an addition salt thereof with a pharmaceutically acceptable inorganic salt or organic salt.

5. A compound of claim 1 being (−)-[diethyl N-(4-O-deacetyl-23-vincristinoyl)-1-amino-2-methylpropylphosphonate], or an addition salt thereof with a pharmaceutically acceptable inorganic or organic acid.

6. A compound of claim 1 being (+)-[diethyl N-(4-O-deacetyl-23-vincristinoyl)-1-aminoethylpropylphosphonate], or an addition salt thereof with a pharmaceutically acceptable inorganic or organic acid.

7. A pharmaceutical composition containing as active principle a compound as claimed in any one of claims 1 to 6, in combination or mixed with a pharmaceutically acceptable non-toxic inert vehicle or excipient.

8. The pharmaceutical composition as claimed in claim 7, containing the active principle in an amount of 0.1 to 100 mg.

9. A method for the treatment of a neoplastic disease of a type known to be responsive to treatment with a vinca alkaloid in a living being comprising the step of administering to the living being an effective amount of a compound of any one of claims 1 to 6, inclusive.

10. A method of claim 9 wherein the compound is administered in the form of pharmaceutical composition thereof in which it is combined with a pharmaceutically-acceptable vehicle or excipient.

* * * * *

UNITED STATES PATENT AND TRADEMARK OFFICE
CERTIFICATE OF CORRECTION

PATENT NO. : 5,100,881
DATED      : Mar. 31, 1992
INVENTOR(S) : Gilbert Lavielle, Patrick Hautefaye, Alain Pierre It is certified that error appears in the above-identified patent and that said Letters Patent is hereby corrected as shown below:

```
Title Page, [75] Inventors:, first line; "Lavielle, Celle"
   should read -- Lavielle, La Celle --.
Title Page [56] References Cited, U. S. PATENT DOCUMENTS, 6th
   listing; "Robinson" should read -- Robison --.
Column 5, line 61; "IV" should read -- VI --.
Column 7, line 52; "sacroma," should read -- sarcoma, --.
Column 19, line 26; "posses" should read -- possess --.
Column 22, line 17; "inorganic salt or organic salt." should read
   -- inorganic or organic acid.--.
```

Signed and Sealed this

Tenth Day of August, 1993

Attest:

MICHAEL K. KIRK

*Attesting Officer*     *Acting Commissioner of Patents and Trademarks*